United States Patent [19]

Lamberti et al.

[11] 4,435,328
[45] Mar. 6, 1984

[54] PREPARATION AND USE OF ALKALI METAL ISETHIONATES FROM ETHIONIC ACID

[75] Inventors: Vincent Lamberti, Upper Saddle River; Wilder F. Pease, Norwood, both of N.J.

[73] Assignee: Lever Brothers Company, New York, N.Y.

[21] Appl. No.: 423,912

[22] Filed: Sep. 27, 1982

Related U.S. Application Data

[62] Division of Ser. No. 270,318, Jun. 4, 1981, Pat. No. 4,369,144.

[51] Int. Cl.³ ........................................... C07C 143/90
[52] U.S. Cl. ...................................................... 260/400
[58] Field of Search ........................................ 260/400

[56] References Cited

U.S. PATENT DOCUMENTS 2,810,745 10/1957 Wolski ................................ 260/504
3,243,454 3/1966 Klass ................................... 260/400
3,320,292 5/1967 Cahn ................................... 260/400
3,637,793 1/1972 van Gysel .......................... 260/400

OTHER PUBLICATIONS

Chemical Abstracts, vol. 81, No. 11, Sep. 1974 by Wooton et al., p. 399.
Chemical Abstracts, vol. 63, No. 1, Jul. 1965, Weinreich et al.
Michael, JACS vol. 58, p. 294, (1936).

*Primary Examiner*—Alan Siegel
*Attorney, Agent, or Firm*—James Farrell

[57] ABSTRACT

The invention discloses a process for the preparation of alkali metal isethionates from ethanol-derived ethionic acid and the use of these isethionates to prepare surface active fatty acyl isethionates. A mixture of calcium hydroxide and alkali metal hydroxide is used to separate the isethionate and the presence of an alkali or an alkali metal soap is required to obtain a light-colored fatty acyl isethionate having a yellowness index less than 10.

9 Claims, No Drawings

PREPARATION AND USE OF ALKALI METAL ISETHIONATES FROM ETHIONIC ACID

This is a divisional application of Ser. No. 270,318 filed June 4, 1981, now U.S. Pat. No. 4,369,144.

This invention relates generally to alkali metal isethionates and more particularly to a process for the preparation of alkali metal isethionates from ethionic acid and the use of these isethionates to prepare surface active fatty acyl isethionates.

Alkali metal isethionates (AMI) are currently made from ethylene oxide and alkali metal bisulfites. Ethylene oxide is a petroleum derived chemical which has recently become more expensive, paralleling the increase in the price of crude oil. The long term outlook is for even higher prices for ethylene oxide as the price of crude oil escalates even further. An alternate method for making AMI from non-petroleum chemicals is, therefore, desirable. Such a process would be even more valuable if AMI could be produced at a lower and more stable cost.

Ethanol is easily available at reasonable cost from natural sources. Furthermore, a process for the conversion of ethanol into ethionic acid is already known (U.S. Pat. No. 3,637,793, incorporated herein, by reference). We now disclose in this invention a practical process for the conversion of ethanol-derived ethionic acid into isethionic acid and a simple, non-toxic method for isolating the isethionic acid as the alkali metal salts. It is, therefore, an object of this invention to provide a method for preparing alkali metal isethionates from ethanol-derived ethionic acid.

Alkali metal isethionates are useful as starting materials in the manufacture of surface active agents (see U.S. Pat. No. 3,320,292). Surface active agents are one of the basic raw materials in the detergent industry. Specifications for such materials generally require the absence of colored impurities in order to prepare high quality, aesthetically pleasant, formulated products such as detergent bars. The use of white or light-colored surface active agents prepared by reducing reactive impurities also minimizes the chance of imparting off-odors to the formulated products.

The hydrolysis of ethionic acid to produce isethionic acid and sulfuric acid has been described in the prior art (see Wooton and Lloyd, J. Org. Chem. 39, 2112 (1974) and Weinreich and Jufresa, Bull. Soc. Chim. France 1965, (3) 787. These references teach that hydrolysis readily occurs under aqueous acid conditions. In the case of the Wooten et al reference, a very dilute solution of ethionic acid ($<1\%$; derived from carbyl sulfate) in 0.01 M sulfuric acid is utilized and sodium isethionate is isolated from the neutralized and dried reaction product by extraction with methanol. In the Weinreich et al reference, an unspecified but substantial dilution is utilized and sulfur dioxide is used initially as a co-solvent. Separation of the isethionic acid thus prepared was then accomplished by two methods: (1) via separation as barium isethionate and conversion therefrom into sodium isethionate by reaction with sodium sulfate and (2) alcoholic extraction of the residue obtained by neutralization of the hydrolysis reaction mixture with sodium hydroxide and evaporation of the water. Similar procedures were utilized by Michael and Weiner, J.A.C.S. 58, 294 (1936).

While the prior art procedures yield the desired sodium isethionate, none of the procedures are conductive to a large scale, economically feasible process because of one or more of the following reasons: (1) hydrolysis conditions are too dilute for practical industrial application, (2) separation procedures employ either soluble barium salts which are toxic and relatively expensive on a stoichiometric basis or solvent extraction which is also expensive, and (3) unforeseen problems, described hereafter, arise during simple scale-up of the desired processes.

When conditions utilized by the prior art methods are modified so as to devise a practical method using higher concentrations of ethionic acid, it is discovered that above a concentration range of about 50%, unhydrolyzed ethionic acid together with impurities such as the bis ether of isethionic acid are encountered even after the solution is vigorously refluxed for several hours. To balance the operating and energy costs with high yields, we found that it is necessary to operate the hydrolysis in the ethionic acid concentration range of about 20–50% and, more preferably in the range of about 20–40%. We also discovered that the isethionic acid can be better separated by employing a mixture of sodium hydroxide and calcium hydroxide whereby a simple one-step separation of sulfuric acid as calcium sulfate and of the isethionic acid as a solution of the desired sodium isethionate is effected. This new method also avoids the use of toxic cations and expensive solvent extraction in the separation scheme.

In addition to the above parameters which were established during working out the optimum operating conditions for the process, it was further found that when the AMI thus produced is reacted with fatty acid to produce fatty acyl isethionates, a dark colored reaction product with a yellowness index (described infra) greater than 10 is obtained. A dark colored product, as explained earlier, is undesirable. We have discovered that the inclusion of an inhibiting amount of alkali or soap in the reaction medium prevents the formation of dark color as will be described more fully hereinafter. It is, therefore, another object of this invention to provide a method for preparing light colored, preferably white or slightly off-white, surface active fatty acid esters of AMI derived from ethionic acid.

Other objects and advantages will appear as the description proceeds.

The attainment of the above objects is made possible by this invention which includes heating an aqueous solution of ethionic acid as a temperature of about 80° C. to about 160° C. for a sufficient time to produce a solution of isethionic acid and sulfuric acid; neutralizing said aqueous solution with a mixture of calcium hydroxide and an alkali metal hydroxide, the amount of said hydroxides in said mixture being sufficient to substantially completely convert the sulfuric acid into hydrated calcium sulfate and the isethionic acid into an alkali metal isethionate, and separating the alkali metal isethionate from said neutralized solution.

Dilution of ethionic acid with a certain amount of water is essential for the hydrolysis reaction. It is desirable to dilute the ethionic acid to a concentration of about 50% or less, preferably 20% to 40%, and most preferably to a concentration of about 35% (w/w) in order to obtain optimum yields. Although dilution less than about 20% gives nearly quantitative yields, the cost of processing the diluted products, e.g., heating to drive off the excess water, becomes uneconomical. At a concentration of about 50% or higher, the amount of unhydrolyzed ethionic acid and the likelihood of the formation of the bisether of isethionic acid substantially increases with a less pure product being obtained. Such an impure product is undesirable for use in the production of fatty acid esters of sodium isethionate for the reasons enumerated above.

After dilution, the ethionic acid is heated at a temperature of about 80° C. to about 160° C. for a sufficient time, usually several hours, to complete the hydrolysis. The rate of reaction being dependent on temperature, the length of heating to accomplish the completion of hydrolysis is accordingly adjusted as should be evident to those skilled in the art. A preferred temperature range is about 100° C. to about 150° C. corresponding to temperatures at which the diluted ethionic acid solution is at or near its boiling point at atmospheric pressure. Of course, pressure higher or lower than the atmospheric pressure can also be employed. The hydrolysis reaction produces an aqueous solution of isethonic acid and sulfuric acid. The isethionic acid and sulfuric acid are usually formed in nearly quantitative yields. The hydrolysis takes place according to the following equation:

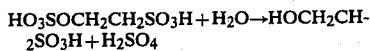

The aqueous solution containing isethionic acid and sulfuric acid is then neutralized with a mixture of calcium hydroxide and an alkali metal hydroxide. A preferred method is first to add a calculated amount of calcium hydroxide equivalent to the amount of sulfuric acid present. The amount of sulfuric acid is calculated on the basis of substantially complete hydrolysis of ethionic acid into an equimolar mixture of isethionic and sulfuric acids. After the addition of the calculated amount of calcium hydroxide, sufficient alkali metal hydroxide, e.g., NaOH, is added so that the pH of the mixture is brought within the range of about 7.0 to 8.5. Using this procedure, the sulfuric acid is converted into hydrated calcium sulfate and the isethionic acid is converted into an alkali metal isethionate. Separation of the desired alkali metal isethionate, e.g., sodium isethionate, from the precipitated hydrated calcium sulfate, is then accomplished by known methods, preferably by filtration of the slurry and washing of the filter cake. The filtrate and the washings contain the desired AMI and a very small amount of hydrated calcium sulfate. The combined filtrate and washings may then be concentrated, for example, to a 50% to 55% solution of AMI. This causes the precipitation of an additional small amount of hydrated calcium sulfate which may then be removed by refiltration or by other known methods.

The concentrated filtrate thus obtained contains substantially quntitative yields of AMI and is free of detectable organic impurities as revealed by NMR analysis. The purity and content of the AMI in the solution was further tested by the conversion of AMI into a fatty acid ester of the alkali metal isethionate (FEI) by reacting the AMI with a fatty acid in the presence of an esterification catalyst. It was found during this process that the FEI product thus obtained from utilizing AMI derived from the ethionic acid as described above, had an undesirable color having a yellowness index greater than 10. We discovered that the addition of a small amount of an alkali or an alkali metal soap inhibited the color formation and gave a desirably light-colored FEI product having a yellowness index less than 10. The yellowness index is measured as follows. A 2.50 g sample of the FEI product is dissolved in 50 ml of a solvent mixture prepared by mixing (volume basis) 30 parts of isopropanol with 4 parts of concentrated hydrochloric acid and 66 parts of distilled water. Using 10 cm cells, the % transmission of the freshly prepared solution is read with a spectrophotometer at 550 nm, 430 nm and 400 nm against the solvent in the reference cell. The yellowness index is then calculated from the expression:

$$\text{Yellowness Index} = 2(T_{550}) - (T_{430} + T_{400})$$

where T is percent transmission at the indicated wavelength.

Although the process of this invention is in essence delineated by the above description, the following examples will more fully illustrate the embodiments thereof. In these examples, as well as the specification and appended claims, parts and percent are by weight unless otherwise indicated.

EXAMPLE 1

Hydrolysis of Ethionic Acid

Ethionic acid, prepared according to the method of U.S. Pat. No. 3,637,793, was diluted with water to form a series of samples of different concentrations of ethionic acid in water. Dilution resulted in a temperature rise from about 25° C. to about 70° C. In the following tests (Table I), samples were refluxed for 3½ hours, then neutralized with 50% sodium hydroxide, freeze-dried and the product analyzed by NMR using neutralized potassium acid phthalate as an internal standard and $D_2O$ as the solvent. The sodium isethionate content (% AMI) is estimated from the area of the chemical shifts at 3.25$\delta$ and 4.05$\delta$ and the area of the chemical shifts for the protons of the internal standard. Unhydrolyzed ethionate is approximated from the area of the group of chemical shifts in the range from about 4.40$\delta$ to 4.70$\delta$. The % yield of AMI is calculated from the % AMI, the total weight of freeze dried product obtained, and the theoretical yield based on the starting quantity of ethionic acid. The results are set forth in Table I.

TABLE I

| Yields of AMI By Hydrolysis of Ethionic Acid At Different Concentrations | | |
|---|---|---|
| % Ethionic Acid Concentration | % Yield of AMI | % Unhydrolyzed Ethionic Acid |
| 19.8 | 94.8 | nil |
| 28.3 | 91.9 | ~1.0 |
| 34.2 | 95.6 | nil |
| 39.8 | 93.2 | 0.5 |
| 50.0 | 95.8 | 2 |
| 50.0 | 93.4 | 1.5 |
| 60.0 | 91.5 | 3.0 |
| 75.0 | — | >4 |
| 75.0 | — | >4 |

The data indicate that an ethionic acid concentration of about 50% or less is desirable with a concentration range of about 20–40% being preferred and about 35% being most preferred. At low concentrations the hydrolysis appears to be slower, indicating that the reaction is acid catalyzed by the sulfuric acid formed during the hydrolysis. Additionally, at low concentrations the AMI product contains excessive amounts of water which has to be evaporated in subsequent processing steps thereby increasing the operating and energy costs. At higher concentration, e.g., about 50%, an equilibrium seems to be established in which the amount of unhydrolyzed ethionic acid increases with increased concentration of sulfuric acid. Higher concentrations also favor the formation of the undesired bis ether of AMI. At about 35% ethionic acid concentration, the hydrolysis is complete in about 2½ hours at atmospheric reflux. It is possible to shorten this time, for instance, by refluxing initially at a 50% ethionic acid concentration for about ¾ of an hour, then diluting the reaction mixture to about 35% ethionic acid and refluxing for about ¾ of an hour longer to establish the desired equilibrium. Other variations to accomplish the desired results are, of course, possible and in view of the instant disclosure will become readily apparent to those skilled in the art. For example, it is possible to operate at higher temperatures utilizing higher than atmospheric pressure thereby reducing the hydrolysis time. Similarly, either a continuous or a batch reaction mode, well known in the art, may be utilized in the practice of this invention.

EXAMPLE 2

Neutralization of Hydrolysis Products

The new method of neutralization of the hydrolysis products of ethionic acid according to the present invention is to add to the hydrolyzed solution a calculated amount of calcium hydroxide approximately equivalent to the sulfuric acid present, and then neutralizing with an alkali metal hydroxide, e.g., NaOH, to a pH of about 7 to about 8.5. When small amounts of sodium sulfate are tolerable in the final AMI product, the amount of calcium hydroxide used is slightly less, e.g., 1-2% less, than the stoichiometric amount required to neutralize the sulfuric acid present. When little or no sodium sulfate is desired in the AMI product, the amount of calcium hydroxide utilized is slightly in excess of the stoichiometric amount required. AMI containing little or no inorganic sulfate, is particularly desirable for making fatty acid esters of AMI that are to be used for making detergent bars. The process for preparing low sulfate containing AMI is described below.

Ethionic acid, 19.40 g, is placed in a 250 ml, round bottom, single neck, flask. Water (36.03 g) is added on top of the cold viscous ethionic acid. Upon swirling the flask, the two layers mix and the temperature climbs to about 70° C. The solution is then heated at reflux for 2½ hours and then cooled. 19.40 g of ethionic acid corresponds to 0.0941 moles and upon complete hydrolysis yields an equimolar concentration of sulfuric acid which requires the same number of moles of calcium hydroxide for neutralization. Powdered calcium hydroxide, 7.19 g (97.92% assay, corresponding to 1% excess over the amount required to neutralize sulfuric acid present) is added to the cold hydrolysis solution while stirring the solution and washing the last trace of the powder into the resulting slurry with a small amount of water. Then NaOH solution (~50%) is added dropwise until the pH of the solution is about 8.5. The slurry is then filtered. The filtration is rapid. The hydrated calcium sulfate filter cake is washed with water. The resulting filtrate containing the desired AMI concentrated to about 50% to 55% AMI. This causes the precipitation of an additional small amount of hydrated calcium sulfate. The solution is again filtered to remove the insoluble hydrated calcium sulfate and then the filtrate is used directly as a source of sodium isethionate. Analysis of the AMI solution thus obtained shows a 97.1% yield of the AMI.

The analysis is carried out by treating a known weight (3 g) of the AMI solution with about 200 g of boiling 95% ethanol and filtering hot to remove the small amount of inorganics present. After washing the inorganics thoroughly with additional hot 95% ethanol, the combined filtrate and washings are evaporated to near dryness. The residue is then taken up in distilled water and quantitatively ion-exchanged by passing through a cation exchange column. The eluate containing the liberated isethionic acid is titrated with standard alkali to determine the amount of isethionic acid present. This amount is then expressed as % AMI basis the weight of the analytical sample (3 g) taken. From the % AMI, the total original weight of AMI solution and the theoretical yield based on the starting ethionic acid, the % yield of AMI is readily calculated.

EXAMPLE 3

Preparation of Sodium Lauroyl Isethionate

The teachings of U.S. Pat. No. 3,320,292 (incorporated herein by reference) are utilized in the reactions described below. Other esterification catalysts may also be used such as those described by Langenbeck et al in Ann. 605, 111-17 (1957) also incorporated herein by reference. Zinc containing compounds are particularly useful since they provide effective catalysis without imparting deleterious effects.

A control run is first prepared for comparison. To a stirred mixture of lauric acid (44.00 g) and zinc oxide (0.070 g) at 155° C. is slowly added 40.62 g of a 53.01% solution of commercial aqueous sodium isethionate prepared from ethylene oxide and sodium bisulfite. A nitrogen purge of about 45 cc/minute is used during the addition, which requires about 18 minutes and during which the reaction temperature continues to increase to about 200° C. Heating is continued for about 10 minutes to a reaction temperature of about 239° C. The nitrogen purge is increased to about 250 cc/minute and the reaction mixture is stirred at about 239° C. for about 90 minutes. The rection mixture is then cooled under nitrogen. During the reaction 4.33 g of lauric acid is distilled leaving in the reaction mixture 39.67 g (0.1980 moles). This corresponds to 1.36 moles lauric acid/mole AMI. Product Analysis: % sodium lauroyl isethionate: 73.2; % conversion of AMI: 89.4; product color: white to slightly off-white, yellowness index: less than 10.

When AMI prepared according to Example 2 above is employed in place of the commercial sodium isethionate using a procedure similar to that described for the control run, a dark colored, tan to brown, FEI product is obtained having a yellowness index greater than 10. Further, the pH of a 1% dispersion of this product in water is about 3.6 compared to about 6.1 obtained for the control run. The acidic reaction product is believed to arise from trace amounts of an unidentified acid precursor, possibly ethionate, in the ethionic acid derived AMI. While not espousing any particular theory, applicants postulate that the reaction conditions (i.e., high temperature, presence of water and fatty acid) liberates traces of sulfuric acid resulting in the low pH and a dark colored FEI product having a yellowness index greater than 10.

To prevent the color formation during the FEI reaction, a sufficient amount of an alkali (e.g., sodium hydroxide) or an alkali metal salt of a carboxylic acid preferably a soap containing from about 8 to about 18 carbon atoms, e.g., sodium laurate, sodium coconut soap or sodium stearate, is added as part of the reaction charge at the beginning of the FEI reaction. The amount of alkali or soap required is small, about 0.2%–2% of the weight of AMI when an alkali, e.g., sodium hydroxide, is used, and about 1–12% of the AMI when a soap, e.g., sodium laurate, is used depending upon the amount of acid precursor present. In this way, the conversion of the AMI into FEI is comparable to the control and the final FEI product is light colored, viz., white to slightly off-white, having a yellowness index of about 10 or less.

It will be understood that the foregoing examples and explanations are for illustrative purposes only and that in view of the instant disclosure various modifications of the present invention will be self-evident to those skilled in the art and are to be included within the spirit and purview of this application and the scope of the appended claims.

We claim:

1. A process for the preparation of a fatty acid ester of an alkali metal isethionate wherein said isethionate is prepared from ethionic acid, comprising the steps of:
   (a) heating an aqueous solution containing about 20% to about 50% of ethionic acid at a temperature of about 80° C. to about 160° C. for a sufficient time to produce a solution of isethionic acid and sulfuric acid;
   (b) neutralizing said aqueous solution with a mixture of calcium hydroxide and an alkali metal hydroxide, the amount of said hydroxides in said mixture being sufficient to substantially completely convert the sulfuric acid into hydrated calcium sulfate and the isethionic acid into an alkali metal isethionate;
   (c) separating the alkali metal isethionate from said neutralized solution; and
   (d) reacting a fatty acid with said alkali metal isethionate in the presence of an esterification catalyst and a sufficient amount of an alkali or an alkali metal salt of a carboxylic acid to form said fatty acid ester of said isethionate, wherein said fatty acid ester has a yellowness index less than about 10.

2. A process as defined in claim 1 wherein said 35% solution is refluxed for 2½ hours at atmospheric pressure.

3. A method of preparing a fatty acid ester of an alkali metal isethionate as defined in claim 1 wherein the amount of said alkali when used is about 0.2% to about 2%.

4. A method of preparing a fatty acid ester of an alkali metal isethionate as defined in claim 1 wherein the amount of said alkali metal soap when used is about 1% to about 12%.

5. A method of preparing a fatty acid ester of an alkali metal isethionate as defined in claim 1 wherein said esterification catalyst contains zinc.

6. A process as defined in claim 1 wherein said alkali metal salt of a carboxylic acid is a soap containing about 8 to about 18 carbon atoms.

7. A process as defined in claim 1 wherein the temperature is about 100° C. to about 150° C.

8. A process as defined in claim 1 wherein said aqueous solution contains about 20% to about 40% ethionic acid.

9. A process as defined in claim 8 wherein said aqueous solution contains about 35% of said ethionic acid.

* * * * *